(12) United States Patent
Sanchez Gil

(10) Patent No.: US 11,801,467 B2
(45) Date of Patent: Oct. 31, 2023

(54) ELECTRONIC MICROBICIDAL AIR FILTER

(71) Applicant: Juan Enrique Sanchez Gil, Valencia (ES)

(72) Inventor: Juan Enrique Sanchez Gil, Valencia (ES)

( * ) Notice: Subject to any disclaimer, the term of this patent is extended or adjusted under 35 U.S.C. 154(b) by 479 days.

(21) Appl. No.: 16/868,559

(22) Filed: May 7, 2020

(65) Prior Publication Data

US 2021/0346830 A1   Nov. 11, 2021

(51) Int. Cl.
| | |
|---|---|
| *B01D 46/00* | (2022.01) |
| *B01D 46/52* | (2006.01) |
| *B01D 46/54* | (2006.01) |
| *A62B 23/02* | (2006.01) |
| *A62B 18/02* | (2006.01) |
| *B01D 53/00* | (2006.01) |
| *A61L 9/20* | (2006.01) |

(52) U.S. Cl.
CPC ......... *B01D 46/0028* (2013.01); *A61L 9/20* (2013.01); *A62B 18/025* (2013.01); *A62B 23/025* (2013.01); *B01D 46/0043* (2013.01); *B01D 46/521* (2013.01); *B01D 46/543* (2013.01); *B01D 53/005* (2013.01); *A61L 2209/14* (2013.01); *B01D 2279/35* (2013.01); *B01D 2279/50* (2013.01); *B01D 2279/65* (2013.01)

(58) Field of Classification Search
CPC ........... B01D 46/0028; B01D 46/0043; B01D 46/521; B01D 46/543; B01D 2279/35; B01D 2279/50; B01D 2279/65; B01D 53/005; A61L 9/20; A61L 2209/14; A62B 18/025; A62B 23/025
See application file for complete search history.

(56) References Cited

U.S. PATENT DOCUMENTS

| | | |
|---|---|---|
| 1,319,763 A | 10/1919 | Drew |
| 3,710,948 A | 1/1973 | Sexton |
| 3,779,244 A | 12/1973 | Weeks |
| 3,802,429 A | 4/1974 | Bird |
| 4,197,100 A | 4/1980 | Hausheer |
| 4,798,676 A | 1/1989 | Matkovich |

(Continued)

FOREIGN PATENT DOCUMENTS

| | | |
|---|---|---|
| KR | 101675826 B1 | * 11/2016 |
| KR | 102171915 B1 | * 10/2020 |

(Continued)

*Primary Examiner* — Robert Clemente
(74) *Attorney, Agent, or Firm* — Hoglund & Pamias, PSC; Roberto J. Rios

(57) ABSTRACT

An electronic microbicidal air filter is provided as an ambient air filter in aeration supports or ventilation grids and as an air filter for PPE protection masks. The filter includes an UVC luminaire (2), a power module (3), activation sensors (4), internal structure (5) with walls defining filtering chambers (6) with exposure membranes (7) sandwiched between the chambers (6) under the luminaire (2), so that the chambers (6) determine a winding zigzag path for the air that passes therethrough, while the particles carried by the air are irradiated by the luminaire (2) directly. The functional elements in the internal structure (5) of chambers (6) are integrated in an encapsulation (9) that surrounds the external part of the assembly and defines a sealed space for the functional and support elements at the ends of the structure (5).

21 Claims, 9 Drawing Sheets

(56) References Cited

U.S. PATENT DOCUMENTS

| | | |
|---|---|---|
| 5,525,136 A | 6/1996 | Rosen |
| 5,747,053 A | 5/1998 | Nashimoto |
| 2005/0163648 A1* | 7/2005 | Liang ................ A61L 9/20 |
| | | 422/186 |
| 2021/0322914 A1* | 10/2021 | Keeler ............... B01D 46/0005 |
| 2022/0096701 A1* | 3/2022 | Pisharodi ............... B64D 13/08 |

FOREIGN PATENT DOCUMENTS

| | | | |
|---|---|---|---|
| KR | 20210115394 A | * | 9/2021 |
| KR | 20220048338 A | * | 4/2022 |
| WO | WO-2021189023 A1 | * | 9/2021 |
| WO | WO-2021204976 A1 | * | 10/2021 |

* cited by examiner

ELECTRONIC MICROBICIDAL AIR FILTER

FIELD OF THE INVENTION

The field of the present invention is directed to the sector of the industry dedicated to the manufacture of filters, focusing particularly on the field of filters intended for the protection against microbial pathogens found in the environment, encompassing, at the same time and in a non-restrictive way, the manufacture of masks and/or face masks, air conditioning devices, ventilation systems for buildings and vehicles, as well as machinery that requires a sterilized environment for the purpose they were designed for.

BACKGROUND OF THE INVENTION

With the economic and commercial development there is a greater number of displacements and said globalization stimulates the spread of the microbial fauna, said fauna is the cause of many pathologies, which require technical and economic attention in order to be neutralized, therefore, we face the need to neutralize these microorganisms so that they are not the motor of social disorders or pathologies in the human body. Aside from these previously described needs, we find the personal needs of individuals with immunodeficiencies, which require controlled and sterile environments, in the same way that certain production processes require equally neutral environments.

Normally we find filters that neutralize certain particles due to their size or by contact with reactive agents that neutralize them, these filters after saturation must be cleaned or discarded, as we can see in previous patents:

- U.S. Pat. No. 1,319,763, issued Oct. 28, 1919, to Drew for "Air filter for wall registers";
- U.S. Pat. No. 3,710,948, issued Jan. 16, 1973, to Sexton for "Self-sustaining 25 pocket type filter";
- U.S. Pat. No. 3,779,244, issued Dec. 18, 1973, to Weeks for "Disposable face respirator";
- U.S. Pat. No. 3,802,429, issued Apr. 9, 1974, to Bird for "Surgical face mask";
- U.S. Pat. No. 4,197,100, issued Apr. 8, 1980, to Hausheer for "Filtering member for 30 filters";
- U.S. Pat. No. 4,798,676, issued Jan. 17, 1989, to Matkovich for "Low pressure drop bacterial filter and method";
- U.S. Pat. No. 5,525,136, issued Jun. 11, 1996, to Rosen for "Gasketed multi-media air cleaner";
- U.S. Pat. No. 5,747,053, issued May 5, 1998, to Nashimoto for "Antiviral filter air cleaner impregnated with tea extract";
- U.S. Pat. No. 5,906,677, issued May 25, 1999, to Dudley for "Electrostatic supercharger screen".

In the patents previously described we can see how after using the filters, they have to be cleaned or destroyed to start a life or use cycle again, therefore, we are faced with filters that become saturated and degraded providing inconveniences in its filtering, and resulting in a residue that in many cases is highly polluting and difficult to destroy.

The pathogen and residues absorption filters are polluting and expendable elements, therefore, there is a double effect of contamination, first in the construction process that must be constant over time if they cannot be cleaned, since they must be replaced with new ones, and in those that can be cleaned, contamination is caused by direct service management and continued over time, these cleaning processes produce a maintenance expense and a detrimental effect in relation to the environment in which the action is performed, as well as on the personnel who carry out said action.

We must consider that many of the filters that are used in the market are built with highly polluting and difficult to manipulate materials.

On the other hand, also with economic and commercial development there is a greater number of displacements and said globalization stimulates the spread of endemic microbial pathogens from all parts of the world, said microbial fauna is the cause of many pathologies, which require medical, technical and economic care to be neutralized, therefore, we face the need to develop high-spectrum protective elements capable of not only protecting us, such as the PPE that currently exists on the market, but addressing such protection from a more advanced point.

In the market there are many masks for personal use, which correspond to different degrees of protection depending on the environments where they are used and keeping a close relationship with the element from which we want to isolate, whether chemical or biological.

The most widespread existing PPE pathogen and/or waste absorption filters for personal use are polluting and expendable elements that produce a double polluting effect, the first in the manufacturing process (constant over time due to its expendability). and the second, after its destruction and/or disinfection, in both cleaning processes produces an environmental and economic expense.

The present invention provides a series of substantial advantages when addressing the environmental filtering process and use in masks, potentially reducing the previously described negative aspects of the operating elements of other known filtering techniques.

SUMMARY OF THE INVENTION

The invention disclosed provides an electronic microbicidal air filter which imparts to its intended function, advantages and characteristics, which will be described in detail below and are an improvement of the current state of the art.

More specifically, the object of the invention is focused on an electronic microbicidal air filter by application of shortwave Ultraviolet-C (UV-C) light for protection and destruction of the harmful capacity of pathogens and chemicals, without the generation of residues or the need for maintenance. The filter is scalable to accommodate the needs of various utilities, specifically in two main types of applications, on the one hand in an application as an ambient air filter, incorporated in aeration supports of air conditioning devices, ventilation grids of buildings and vehicles, as well as machinery ventilation grids that require a sterilized environment for the purpose they were designed for, and, on the other hand, in an application as an air filter for PPE protection masks and/or face masks.

BRIEF DESCRIPTION OF THE DRAWINGS

In order to complete the description being made and to ease a better understanding of the characteristics of the invention, we attach to the present specification, making part of the same, a set of layouts where, with an illustrative non limitative character, the following has been represented.

DETAILED DESCRIPTION OF THE INVENTION

Figure 1:
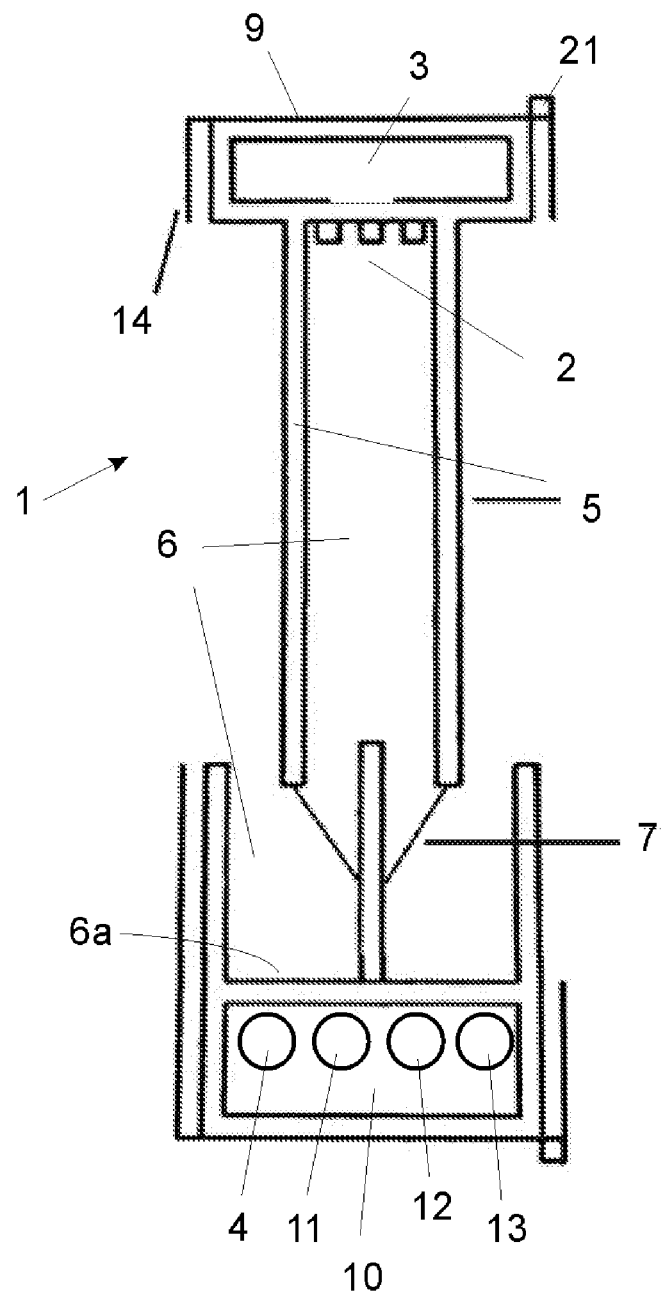
FIG. 1 shows a schematic representation of a section in perpendicular section of an exemplary filter according to the invention, specifically as a minimum filtering module.

The electronic microbicidal air filter that the invention proposes, as previously indicated, works by applying UV-C light (shortwave) for protection and destruction of pathogens and chemicals, without generating residues or needing maintenance, being scalable for accommodate various applications such as, masks and/or face masks, aeration supports for air conditioners, ventilation grids for buildings and vehicles, or machinery ventilation grids that require a sterilized environment.

For this, and more specifically, the filter of the invention is distinguished by essentially comprising an UVC luminaire, a power module for said luminaire, a lower compartment for housing batteries, sensors, resistors and a charging module, all integrated in a structure that defines various chambers therein, which are scalable depending on the filtering needs that are required, but which in any case define a winding passage with interspersed exposure membranes, strategically located under the luminaire, and a bottom over the lower compartment.

In addition, these chambers may be configured in two ways; first by free filtering chambers, without micro-fans, and/or second, by assisted filtering chambers with micro-fans. The incorporation or not of said micro-fans is also adjustable to the required filtering needs.

In any case, the internal structure of the filter provides a succession of chambers arranged together in a zigzag manner, which forces the air to advance through each of the chambers, in turn passing through the exposure membranes where the UV-C light beam of the luminaire falls, directly.

By advancing air through these chambers, what is produced is an exposure of said air to the effect of UV-C shortwave ultraviolet light, which affects the microorganisms in the environment causing severe damage to their DNA and preventing said microorganisms from reproducing, preventing them from being harmful.

In the same way, after passing the air through each of the chambers, any heavier volatile element, such as small liquid microparticles, are precipitated at the bottom of the filter, either due to the direct effect of the volatile element path or due to the effect of gravity by draining said moisture or liquid through the different internal walls of the structure that makes up the filter.

Once the possible humidity is precipitated, it will be neutralized and sterilized, also by the effect of UV-C light and at the same time, it will periodically evaporate when resting in the bed of a radiant floor, whose heat is established by the reflection of the heat given off by a resistor that the filter has, in a preferred embodiment, housed in the compartment at the bottom thereof, where, in turn, are housed the sensors or detectors that operate the UV-C lamps on the upper part and, where appropriate, the micro-fans.

Optionally, it is also established the possibility of accommodating batteries, especially in its application as a filter for a mask, or in its application as a filter for air or ventilation devices if it does not have a constant electrical supply, and if it is not required, these batteries can be omitted and the filter can be connected to the external current in both its direct or alternating aspects, replacing the batteries with the power module.

Therefore and as a summary of the operation of the filter, the air passes through the filter, the effect of the shortwave of ultraviolet light, and the lower resistors, provide the eradication of any residue that may exist, sterilizing the air that is crossed by the filter, so there are no residues to remove, nor is there any harmful element as a result of filtering, it is an automatic, autonomous filter with a neutral microbial load.

The aforementioned elements, together with the structure that defines the zigzag chambers that guide the air through the filter, preferably, comprise an external part that surrounds the assembly and forms a plastic encapsulation. The composition and characteristics of said encapsulation, as well as its configuration, will depend on the requirements that are required in each application, with ABS or PVC being one of the most widely used, but it is possible to opt for others more in line with the design expectations of the apparatus, device or element where the filter is to be housed, which, as has been said, can be used both for an air conditioning or ventilation apparatus or the like, as well as for a protective mask or face mask, in which case, said encapsulation will be made of a softer material, for example silicone and, logically, with the corresponding scaling of the dimensions of its elements.

In any case, once all the internal elements of the filter are encapsulated, it will be sealed, so that it cannot be manipulated or modified, it is therefore a long-lasting element, around 50,000 hours of lifetime of the filter, which, once the threshold of optimal use has been exceeded, it will be removed and each of the filter elements can be recycled without problems, without the need for any relevant previous step and with all the guarantees of safety.

In an embodiment, in which the filter is intended for an air or ventilation apparatus, on its external part, the filter will have, as an external structural element, a ring made of plastic material or metal foil, where will be placed a silicone seal that acts as an airtight element in relation to the niche where the filter is intended to be housed, achieving a perfect tightness and not allowing air to pass through an area that could not be filtered.

Continuing with the particularities of the invention, in another embodiment, the filter is applicable for incorporation into a mask, for example a one-person PPE mask, which can be of variable configuration and structure, so it should not be taken restrictively and therefore, it is possible to apply the filter to different aesthetic models of masks.

In any case, it includes, as already described, an encapsulation inside which the electronic microbicidal filter is housed, encapsulated which, in turn, is housed inside a fastening and sealing support that, preferably, is manufactured with a plastic element, preferably silicone, to provide the necessary elasticity to keep the encapsulation fixed therein by exerting a stretching effect on the material, to introduce it therein or remove it therefrom.

The flow of inhaled or exhaled air, which is introduced into the filter by normal use, is neutralized and freed from the harmful action of pathogens due to sterilization after exposure to UVC light from the luminaire contained in the filter.

Therefore and as a summary of the operation of the mask, the air passes through the filter subjecting it bidirectionally to the effect of the shortwave of UV-C ultraviolet light, with no residue to remove, and without any harmful element remaining as a result of the filtering, such that the mask, when incorporating the electronic microbicidal filter, is automatic and autonomous, since the mask has internal batteries that supply power to the UVC luminaire to achieve the neutralization of pathogens autonomously and automatically when operating exclusively when it is being used, by detecting said use through the sensors also provided therein, which determine the need to apply said light, exclusively in use, all thanks to its incorporation into the mask of the filtering system object of the invention.

As already mentioned, in this case of applying the filter in a mask, the composition of the external part that surrounds each of the functional elements of the filter, as well as the structure that defines the zigzag chambers that guide the air through the filter, is made of soft plastic, in order to ensure the protection of the individual against falls, avoiding physical damage to the person who uses it, and ensuring at the same time that there are no cracks due to blows in the structure of the filtering system.

The fastening system of the encapsulation is preferably made of silicone, providing full adherence to the filter that is housed therein and, in turn, having a 1cm long lip on its external part, which produces a tightness effect. between the filter, the nose and the mouth, not allowing unfiltered air to enter.

To use the mask, first of all, you can choose the model you want to use in relation to aesthetic or morphological aspects, once the mask is defined, the encapsulation is placed inside the support, and in turn, everything is placed inside an internal pocket provided for this purpose in the mask as a space to receive it. Previously, the encapsulation must have been loaded into the electrical grid so that it has sufficient autonomy, and then the mask can be used as any other, ensuring that the internal lips of the fastening membrane that project to the nose and mouth are well positioned and adjusted, producing a suction cup or tightness effect.

In any case, the descriptions of the aforementioned elements must be interpreted in a broad and non-restrictive way, therefore, the materials of which the filter is composed are adaptable to the requirements of where there are intended to be housed, maintaining the same system and disinfection process scheme, in this way, for example for its application in air or ventilation devices, micro-fans can be incorporated or not, and a different plastic can be used for the encapsulation of the elements and the construction of the air guide internally, as well as sizing the filter according to the number of luminaires and filtering cells and external size. Likewise, batteries can be adapted for use without an electrical connection or a transformation module can be installed to connect to the electrical current.

And, for its part, for the application of the filter in a mask, the materials of which the encapsulation, fastening membrane or mask are composed, are adaptable to the requirements of utility and functionality, as well as to possible substitutions with novel materials that could be useful for said application and, in the same way, batteries with more or less capacity can be adapted for different uses, being able, if necessary, to incorporate a solar charging module, if the conditions of use were extreme and if commercially, it would be interesting to provide this PPE disinfection unit with such a characteristic.

In short, the object of the invention is a filter with the described characteristics, regardless of the shape or dimensions that the filter may have, which will correspond to the needs of the application wherein it is intended to locate or place, and therefore, it will physically adapt in its structural aspect taking very diverse shapes such as round, triangular, irregular etc., and in the same way the filter materials will be adapted to the exposure environments, considering temperature, humidity and other physical parameters when determining the filter structural composition.

The object of protection is therefore a filter for filtering the air through the guiding thereof through a duct, producing by means of said passage an exposure close to a UV-C light beam with the intention of sterilizing said air and causing with this same act a potential reduction of the harmful effects that there are or that may be in a certain air flow that is intended to be filtered, and all this, without a maintenance action being necessary after using the filter, and without that the effect of filtering produces residues that must be treated later.

In the same way, what is also intended to protect is the installation of the electronic microbial filter for use in masks designed for this purpose, which establishes a fundamental novelty, which is that an personal protection effect is produced by means of exposure of the breathed air to a beam of UV-C shortwave ultraviolet light producing two results:

1) The protection of the individual from microbial and chemical agents, by means of air sterilization and therefore, in the same way, destroys the harmful substance without producing any by-product from use; and
2) The destruction of the pathogen or chemical found in the environment and therefore, reducing the possibility of contamination to third parties, eradicating said element from the environment.

The shape or dimensions that the encapsulation of the mask or of the support can have, which will correspond to the needs of the air flow that is intended to filter, which can be variable, depending on the region or weather condition where you want to use it, in any case, the essential feature of the invention is the method by which the electronic microbial filter is attached to a mask that at the same time is attached to the face of a user and filters the air breathed that is irradiated by a UV-C beam for sterilization, once the materials more or less appropriate to the environment of use have been determined.

To avoid a possible lack of clarity, it is convenient to clarify the sense of the meaning of some of the terms used in the description. The term "microorganisms" includes without limitation bacteria, protozoa, viruses, moulds, and the like. Dust mites are also included in this definition, so the term is to be understood broadly and not restrictively. The expression "microbial pathogen" is intended to refer to a microscopic living being that, after exposure thereto, causes or may cause damage to the body that it invades directly or indirectly. As named herein, the term "dimerization" is understood as the process by which a chemical reaction occurs in which two molecules of identical subunits (monomers) form a single chemical structure, called a dimer. The word "microbicidal" is intended to describe an element capable of neutralizing the harmful consequences that microorganisms could produce when coming into contact with the object to be protected. The acronym PPE refers to the definition of a personal protective element.

In light of the mentioned figures, and according to the numbering taken on them, can be seen in them an example of non-limiting realization of the electronic microbicidal air filter of the invention, which includes what is indicated and described in detail below.

Thus, as can be seen in FIG. 1, the filter (1) in question essentially comprises at least one UVC luminaire (2), a power module (3) for said luminaire (2), and activation sensors (4), coupled to an internal structure (5) with walls that define various filtering chambers (6) therein with exposure membranes (7), sandwiched between said chambers (6) and which are located under the luminaire (2), such that the chambers (6) determine a winding zigzag path for the air that passes through the filter (1), while the particles carried by said air are irradiated by the luminaire (2) directly.

Furthermore, preferably, the internal structure (5) of chambers (6) also defines a lower bottom (6a) on the surface of which any heavier volatile element of air is deposited, when passing through said chambers (6).

Figure 2:
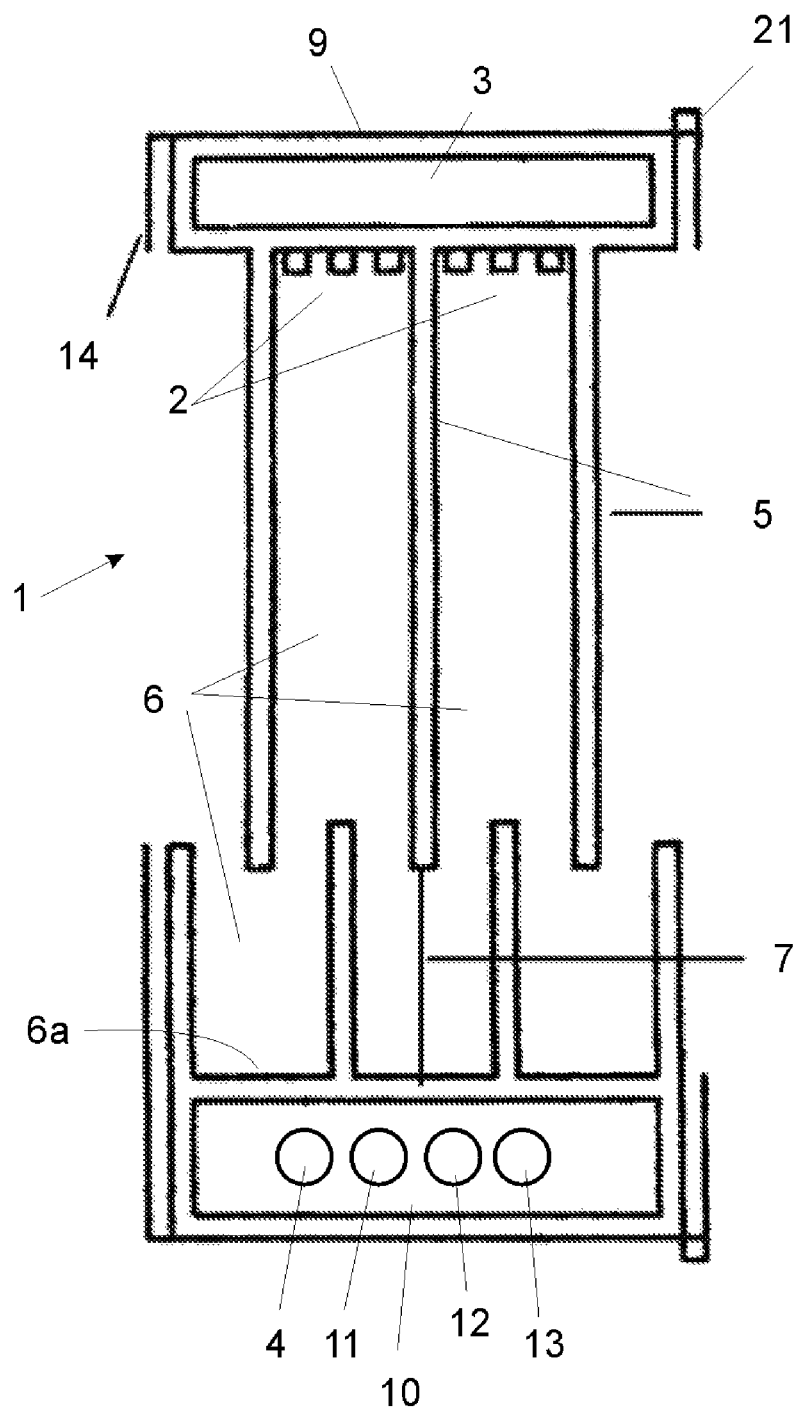
FIG. 2 shows a schematic representation of a perpendicular section of another example of the filter of the invention, as an expanded module.

In FIG. 2 can be seen how the configuration of the internal structure (5) with walls that define the chambers (6) inside the filter (1) can vary, depending on each application, and therefore can have more or less number of said chambers (6) as well as different arrangement and number of exposure membranes (7) and also more than one UVC luminaire (2).

Figure 3:
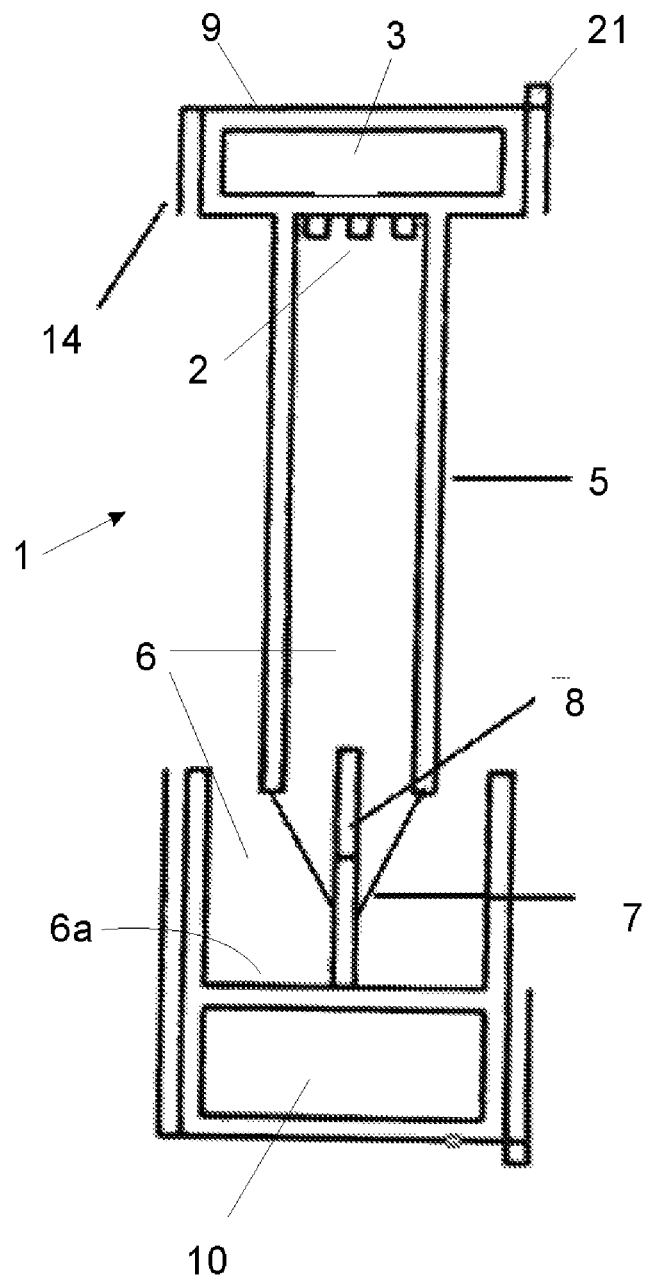
FIG. 3 shows a schematic representation of a perpendicular section of yet another example of the filter of the invention, with micro-fans in the filtering chamber.

Referring to FIG. 3, it can be seen how, in addition, in an embodiment of the filter (1), said chambers (6) can include micro-fans (8) sandwiched between some of them to provide air filtering with assisted flow.

In any case, both the internal structure (5) of chambers (6) and all the functional elements described are integrated in an encapsulation (9) that surrounds the external part of the assembly and defines a sealed space for said functional and support elements at the ends of said structure (5) where, preferably, an upper part incorporates the power module (3), in contact with the luminaire (2), and the lower part, under the bottom (6a) of the chambers (6), forms a compartment (10) for the sensors (4) and other components.

Thus, in an embodiment of the invention, preferably a form applicable as a filter for air conditioning or ventilation apparatus, the filter (1) further comprises a resistor (11) housed in the compartment (10), providing radiation to evaporate possible heavy elements deposited in the bottom (6a) of the chambers (6).

Optionally, said compartment (10) also incorporates at least one battery (12) and a charging module (13) that can replace or be complementary to a mains electrical supply connection of the power module (3), making the filter an element completely autonomous, without ruling out, optionally, the inclusion of a solar panel connected to the power module (3).

It should be noted that, although only FIGS. 1 and 2 have schematically represented the components or functional elements of the filter (1) that are housed within the compartment (10) that internally defines the encapsulation (9), it should be taken as a non-limiting example, being able to include only one, several or all of them, in any case, at least one sensor (4).

Figure 4:
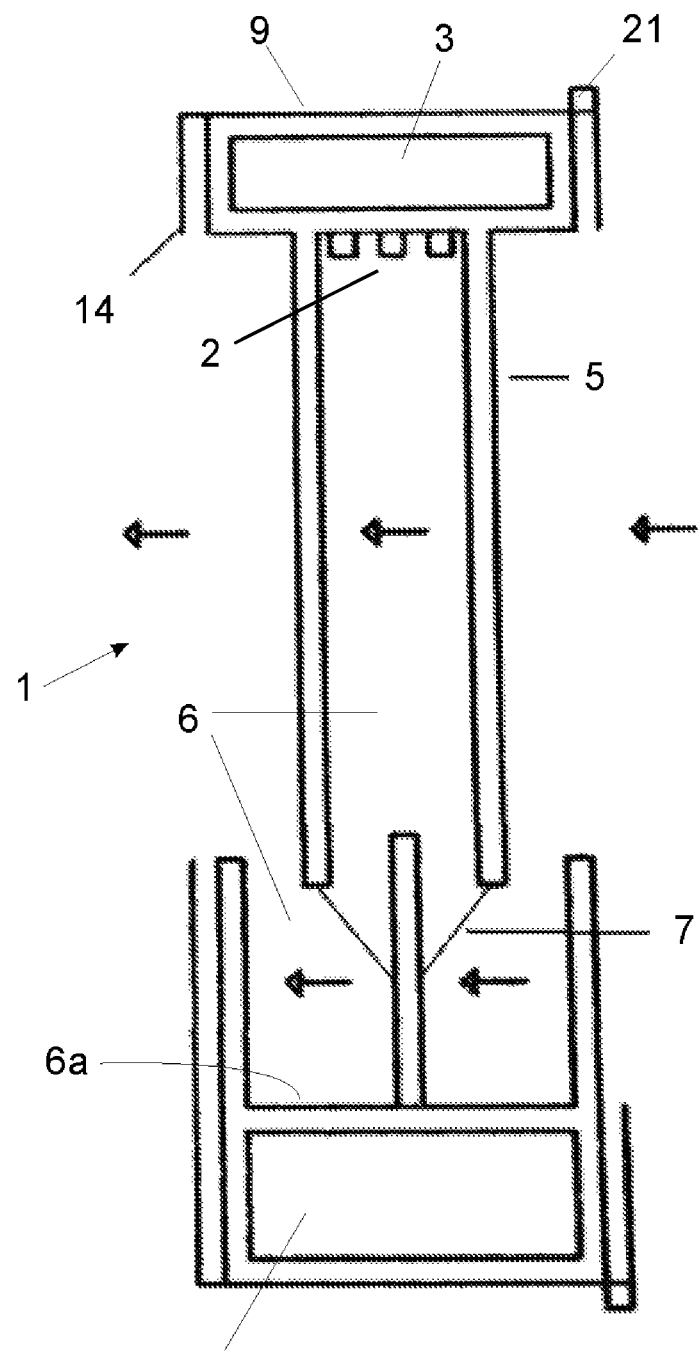
FIG. 4 shows a perpendicular section of the exemplary filter shown in FIG. 1, including by means of arrows a representation of the evolution of the air flow within the filter.
Figure 5:
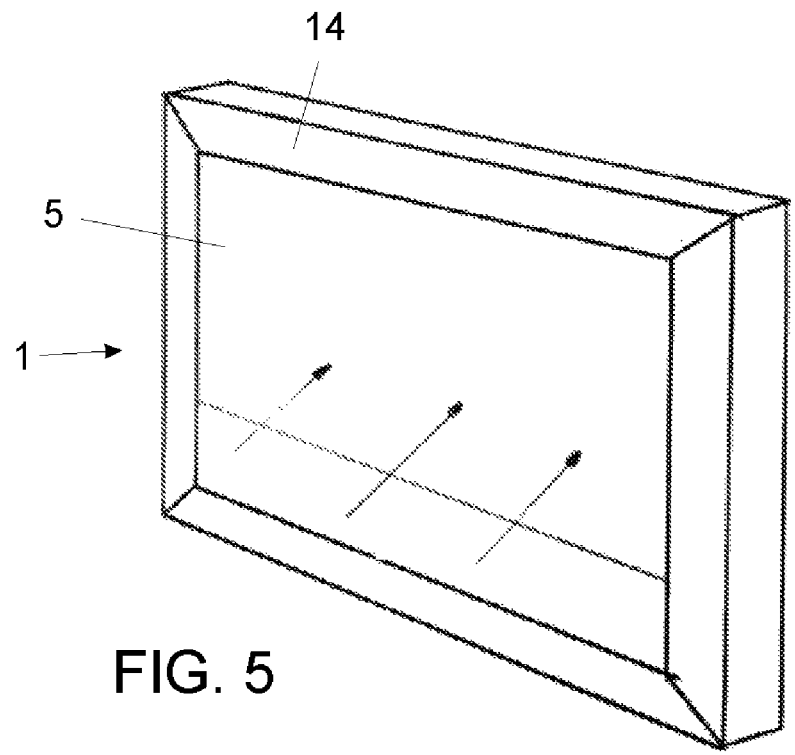
FIG. 5 shows a perspective view of a schematic representation of the filter in its external appearance, in a form thereof applicable to air or ventilation apparatus for filtering ambient air.
Figure 6:
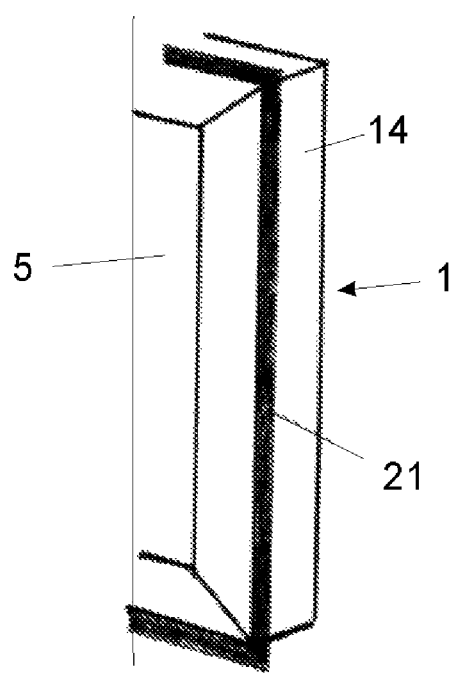
FIG. 6 shows a partial view of the representation of the filter shown in the FIG. 5 with the inclusion of the seal.

In an embodiment, in which the filter is intended for an air or ventilation apparatus, the encapsulation (9) of the filter is preferably a plastic material such as ABS or PVC, although this is not a limitation. And, as can be seen in FIG. 5, it is preferably incorporated into an external structural element (14) consisting of a ring made of plastic material or metal sheet, where a silicone seal (21) will be placed, which acts as an airtight element in relation to the compartment where the filter (1) is intended to be housed, as shown in FIGS. 5 and 6. In this application form, the air flow through the filter (1) is unidirectional, as represented by arrows in FIGS. 4 and 5, passing through the chambers (6) that define the interior structure (5) with walls, from one side to the other.

Figure 7:
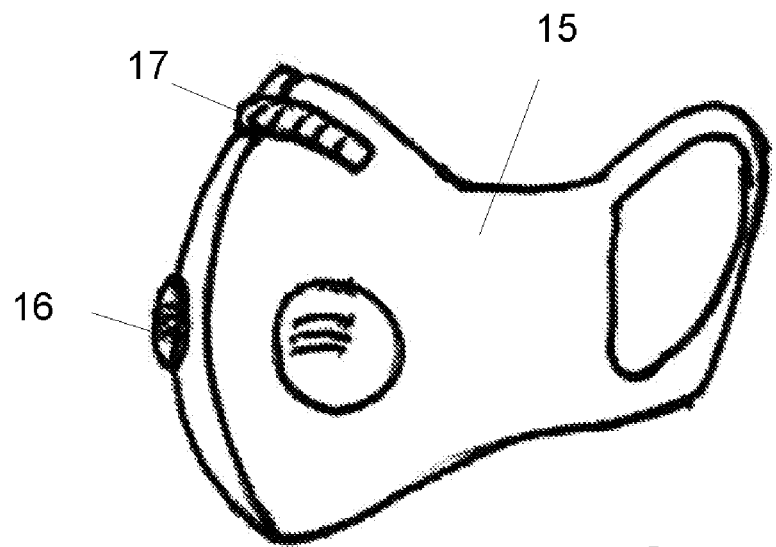
FIG. 7 shows a schematic perspective view of an example of a mask to which the filter of the invention is implemented in its other form of application.
Figure 10:
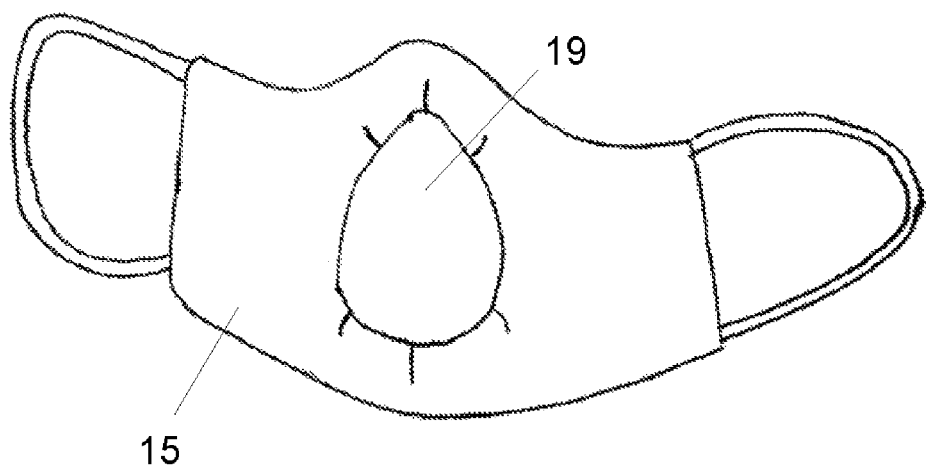
FIG. 10 shows a perspective view of the internal part of the mask, prior to the incorporation of the filter, being appreciated the space with the interior pocket provided therefor.
Figure 11:
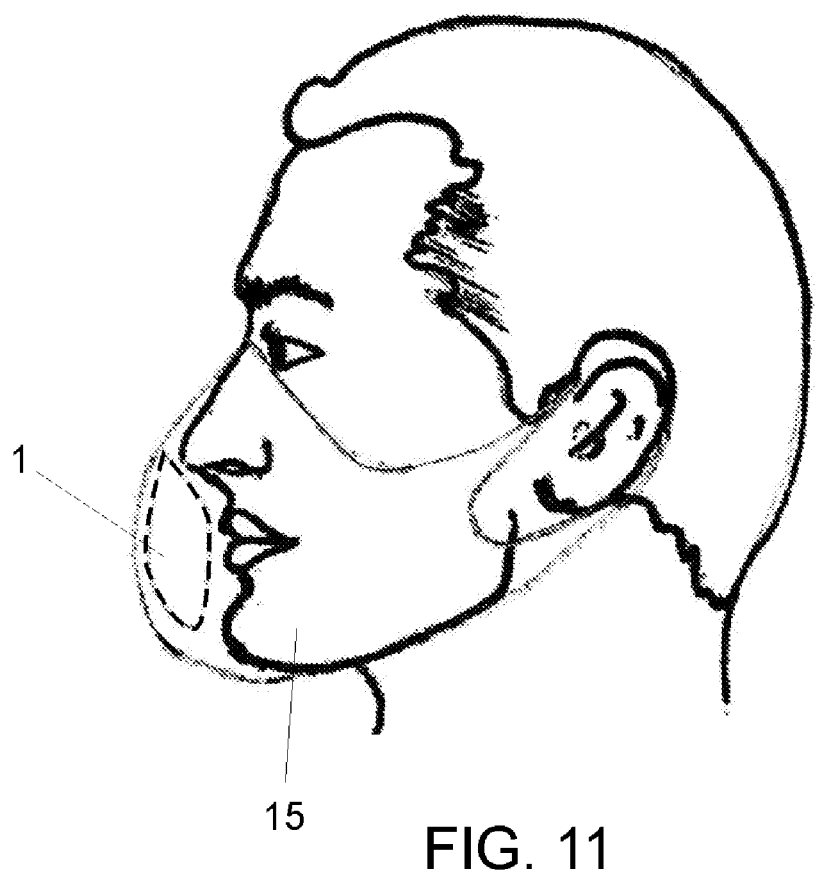
FIG. 11 shows an elevation view of a user with the mask on, showing the position of the filter therein.

On the other hand, according to FIGS. 7-12, another embodiment of the filter (1) can be seen, in this case applicable as a filter element for incorporation into a mask (15), for example a one-person PPE mask, such like the one shown in FIG. 7, consisting of a conventional mask, where in addition to the mask (15) itself, it comprises a garnish (16) and an adjustment element (17) for fastening to the nose and inside which it attaches the filter (1) of the invention, as seen in FIG. 11, it should be understood that said mask (15) can vary in shape and structure.

Figure 12:
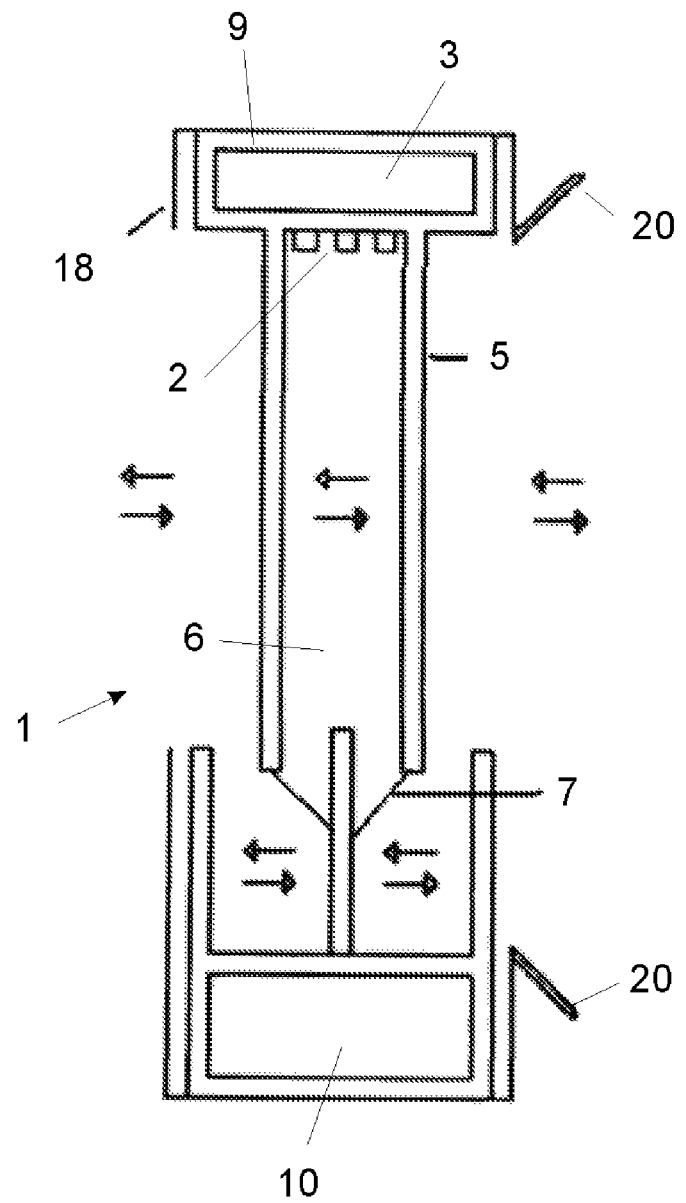
FIG. 12 shows a schematic representation of a perpendicular section of the filter as applied to the mask, showing the lips of the fastening support and, by means of arrows, a representation of the air flow through the filter bidirectionally.

In any case, the filter (1) in this case comprises a luminaire (2), a sensor or sensors (4), a power module (3) and a battery (12) housed in an encapsulation (9) with an internal structure (5) that defines chambers (6) with exposure membranes (7) sandwiched therebetween under the luminaire (2), so that the chambers (6) determine a winding zigzag path for the air passing therethrough, in this case in a bidirectional sense, that is, from the inside to the outside and from the outside to the inside, as indicated in FIG. 12, and where thanks to the battery (12) providing the power supply to the UVC luminaire (2), the neutralization of pathogens is achieved autonomously and automatically, by operating exclusively when it is being used, by the detection of said use through the sensors (4).

Figure 8:
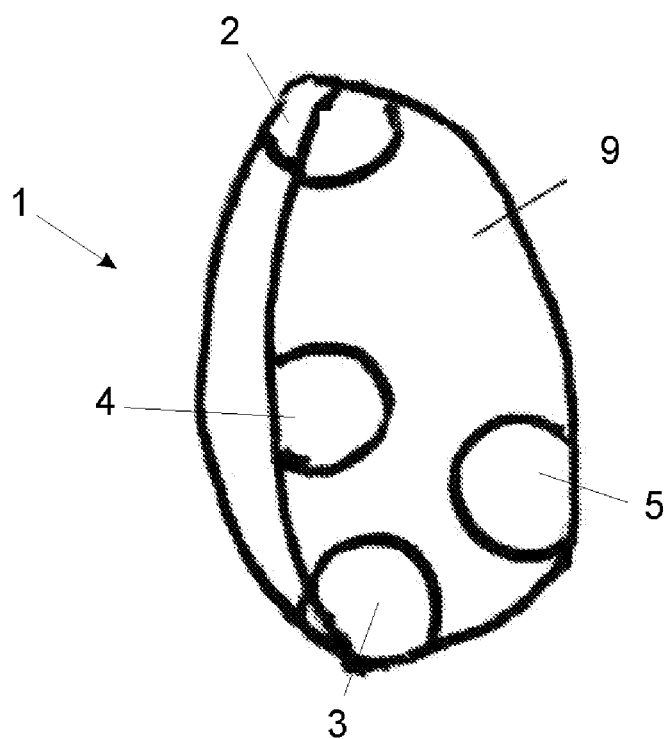
FIG. 8 shows a perspective view of a schematic representation of the filter applicable to the mask with its encapsulation.
Figure 9:
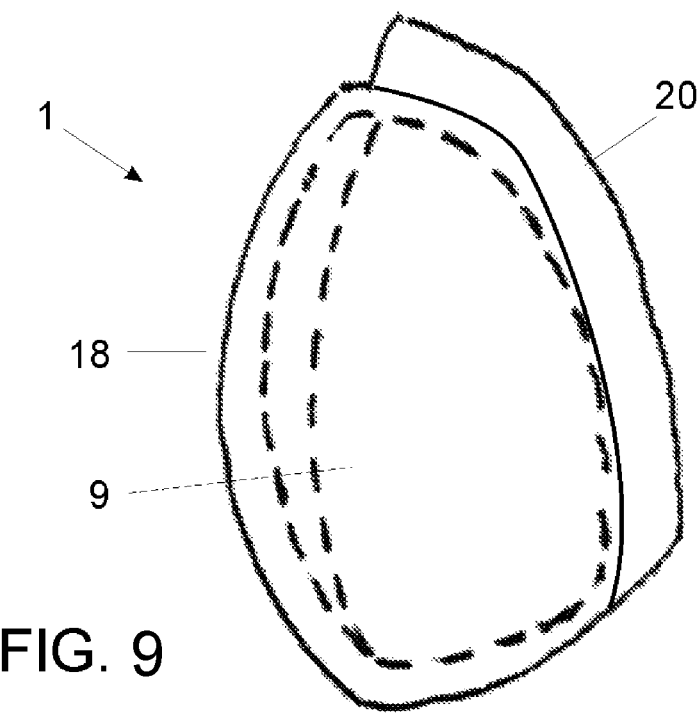
FIG. 9 shows a perspective view of a representation of the encapsulated filter shown in FIG. 7 housed in the silicone support.

Preferably, the encapsulation (9), which is preferably made of silicone or a similar soft material, in turn, is housed inside a fastening and sealing support (18) which, preferably, is also made of soft plastic material, preferably silicone, it has a cup-shaped configuration, as seen in FIG. 8, suitable for incorporation inside the mask (15) which, preferably, is provided with an internal pocket (19) to fix its positioning, as shown in FIG. 10.

Furthermore, in the preferred embodiment of the filter (1) as applied in a mask (15), said encapsulation (9) has, on its external part, a lip (20) that, as seen in FIG. 12, emerges around its contour to fit the user's face, around the nose and mouth, and produce a tightness effect between the filter (1) that does not allow the passage of unfiltered air.

Having sufficiently described the nature of the present invention, as well as a way of putting it into practice, it is not considered necessary to make a more extensive explanation in order that any expert in this area will understand its scope and the advantages that can be derived from it, making known that, within reason it could be put into practice in other embodiments differing in detail from that indicated by way of example, and which will obtain the same degree of protection, provided that they do not alter, change, or modify its fundamental principle.

The invention claimed is:

1. An electronic microbicidal air filter comprising:
an internal structure (5) housing at least one UVC luminaire (2), a power module (3) connected to said luminaire (2) and at least one activation sensor (4), wherein said internal structure (5) includes walls defining filtering chambers (6) located below said at least one UVC luminaire (2) and having membranes (7) provided between said filtering chambers (6), the filtering chambers (6) being positioned to define a winding zigzag path for air that passes therethrough where micro-fans (8) are positioned between the filtering chambers (6) to filter air with assisted flow, while particles carried by the air are directly irradiated by the at least one UVC luminaire (2); and
an encapsulation (9) housing said internal structure (5), wherein said encapsulation (9) surrounds said internal structure (5) to define sealed spaces at opposing ends thereof.

2. The electronic microbicidal air filter according to claim 1, wherein said internal structure (5) includes a lower bottom (6a) for depositing heavy volatile elements contained on air.

3. The electronic microbicidal air filter according to claim 2, wherein said encapsulation (9) has an upper sealed space containing said power module (3) which is electrically coupled to the luminaire (2), and a lower sealed space provided under the lower bottom (6a) of the filtering chambers (6) which forms a compartment (10) housing said at least one activation sensor (4).

4. The electronic microbicidal air filter according to claim 2, further comprising a resistor (11) providing radiation to evaporate said heavy volatile elements.

5. The electronic microbicidal air filter according to claim 4, wherein said resistor (11) is housed in the compartment (10).

6. The electronic microbicidal air filter according to claim 1, further comprising at least one battery (12) and a charging module (13).

7. The electronic microbicidal air filter according to claim 6, wherein said at least one battery (12) and said charging module (13) are housed in the compartment (10).

8. The electronic microbicidal air filter according to claim 1, further comprising a solar panel connected to the power module (3).

9. An electronic microbicidal air filter applicable as an ambient air filter, incorporated in aeration supports of air conditioning devices, ventilation grids for buildings and vehicles, and machinery ventilation grids, said electronic microbicidal air filter comprising:
at least one Ultraviolet-C(UVC) luminaire (2);
a power module (3) electrically connected to said at least one UVC luminaire (2);
at least one activation sensor (4);
an internal structure (5) having walls defining filtering chambers (6) located below said at least one UVC luminaire (2) and having membranes (7) provided between said filtering chambers (6), wherein said filtering chambers (6) are positioned to define a winding zigzag path for air that passes therethrough, while particles carried by the air are directly irradiated by the at least one UVC luminaire (2), said internal structure (5) being integrated in an encapsulation (9) that defines sealed spaces at opposite ends of said internal structure (5), wherein one sealed space incorporates the power module (3) and another opposite sealed space forms a compartment (10) housing the at least one activation sensor (4); and
an external structural element (14) incorporating said encapsulation (9) and comprising a ring of plastic material or metal sheet.

10. The electronic microbicidal air filter according to claim 9, further comprising micro-fans (8) positioned between the filtering chambers (6) to filter air with assisted flow.

11. The electronic microbicidal air filter according to claim 9, wherein the internal structure (5) includes a lower bottom (6a) positioned above said compartment (10) which in turn housing a resistor that provides radiation to evaporate heavy elements deposited on said lower bottom (6a).

12. The electronic microbicidal air filter according to claim 9, further comprising at least one battery (12) and a charging module (13) housed in said compartment (10).

13. The electronic microbicidal air filter according to claim 9, further comprising a solar panel connected to the power module (3).

14. The electronic microbicidal air filter according to claim 9, wherein the encapsulation (9) is made of plastic material.

15. The electronic microbicidal air filter according to claim 9, further comprising a silicone seal (21) acting as an airtight element in relation to a niche where the filter is housed.

16. An electronic microbicidal air filter, applicable as an air filter for PPE masks and/or face masks comprising:
an internal structure (5) housing at least one luminaire (2), at least one sensor (4), a power module (3) and at least one battery (12), wherein said internal structure (5) defines chambers (6) having membranes (7) provided between the chambers (6) under the at least one luminaire (2), so that the chambers (6) are positioned to define a winding zigzag path for air that passes therethrough, while particles carried by the air are directly irradiated by the at least one luminaire (2); and
an encapsulation (9) made of soft material housing said internal structure (5), said encapsulation (9) being in turn housed inside a fastening and sealing support (18) suitable for incorporation inside a mask (15).

17. The electronic microbicidal air filter according to claim 16, wherein the encapsulation (9) is made of silicone.

18. The electronic microbicidal air filter according to claim 16, wherein the fastening and sealing support (18) is made of soft plastic material.

19. The electronic microbicidal air filter according to claim 18, wherein the fastening and sealing support (18) is made of silicone.

20. The electronic microbicidal air filter according to claim 16, wherein the encapsulation (9) has on an external part, a lip (20) configured to tightly fit around a nose and a mouth of a user.

21. The electronic microbicidal air filter according to claim 16, wherein the fastening and sealing support (18) is incorporated in an internal pocket (19) provided on said mask (15).

* * * * *